US00PP33055P2

(12) United States Plant Patent
Griffin

(10) Patent No.: US PP33,055 P2
(45) Date of Patent: May 11, 2021

(54) ***ALOE* PLANT NAMED 'SNOW DRIFT'**

(50) Latin Name: ***Aloe* hybrid**
Varietal Denomination: SNOW DRIFT

(71) Applicant: Altman Specialty Plants, Inc, Vista, CA (US)

(72) Inventor: Kelly Griffin, Carlsbad, CA (US)

(73) Assignee: Altman Specialty Plants, Vista, CA (US)

( * ) Notice: Subject to any disclaimer, the term of this patent is extended or adjusted under 35 U.S.C. 154(b) by 0 days.

(21) Appl. No.: 16/873,343

(22) Filed: Mar. 24, 2020

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Aloe* plant named 'SNOW DRIFT' is disclosed, characterized by an upright growth habit, light greyed-green leaves, and red flowers. The new variety is an *Aloe*, typically produced as a garden or container plant.

2 Drawing Sheets

Latin name of the genus and species: *Aloe* hybrid.
Variety denomination: 'SNOW DRIFT'.

BACKGROUND OF THE INVENTION

The new cultivar is a product of a planned breeding program. The seed parent is the unpatented *Aloe* 'Moon Dance'. The pollen parent is an unpatented, unnamed, proprietary seedling resulting from the crossing of *Aloe rauhii*, x *Aloe inermis* x *Aloe* 'White Lightning'. The crossing resulting in 'SNOW DRIFT' was made in December 2016 at a commercial greenhouse in Vista, Calif. 'SNOW DRIFT' was found and selected by the inventor in May 2017 at the same greenhouse in Vista, Calif.

Asexual reproduction of the new cultivar 'SNOW DRIFT' was first performed by tissue culture at a commercial laboratory in Vista, Calif. in July 2017. 'SNOW DRIFT' has since produced several generations and has shown that the unique features of this cultivar are stable and reproduced true to type.

SUMMARY OF THE INVENTION

The cultivar 'SNOW DRIFT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SNOW DRIFT'. These characteristics in combination distinguish 'SNOW DRIFT' as a new and distinct *Aloe* cultivar:

1. Upright growth habit.
2. Light Grey-Green leaves with a faint pink flush.
3. Red flowers.
4. Table top size *Aloe*, maturing to 8" across.

PARENTAL COMPARISON

Plants of the new cultivar 'SNOW DRIFT' are similar to the seed parent in most horticultural characteristics. However, plants of the new variety differ from the seed parent in the following:

1. The new variety has a more compact, upright rosette than the seed parent.
2. The new variety has smoother leaf edges than the seed parent.

Plants of the new cultivar 'SNOW DRIFT' are similar to the pollen parent in most horticultural characteristics. However, plants of the new variety differ in the following:

1. The parent variety has solid colored leaves, the new variety has speckled leaves.

COMMERCIAL COMPARISON

'SNOW DRIFT' can be compared to the unpatented commercial variety *Aloe* 'White Lightning'. The two *Aloe* varieties are similar in most horticultural characteristics; however, the new variety differs in the following:

1. The new variety is a larger, more open plant than this comparator.
2. The new variety has a smoother leaf margin than this comparator.
3. The new variety produces light greyed-green leaves at all light levels
4. The new variety has a cleaner, more symmetrical growth habit than this comparator.

BRIEF DESCRIPTION OF THE PHOTOGRAPHS

Figure 1:
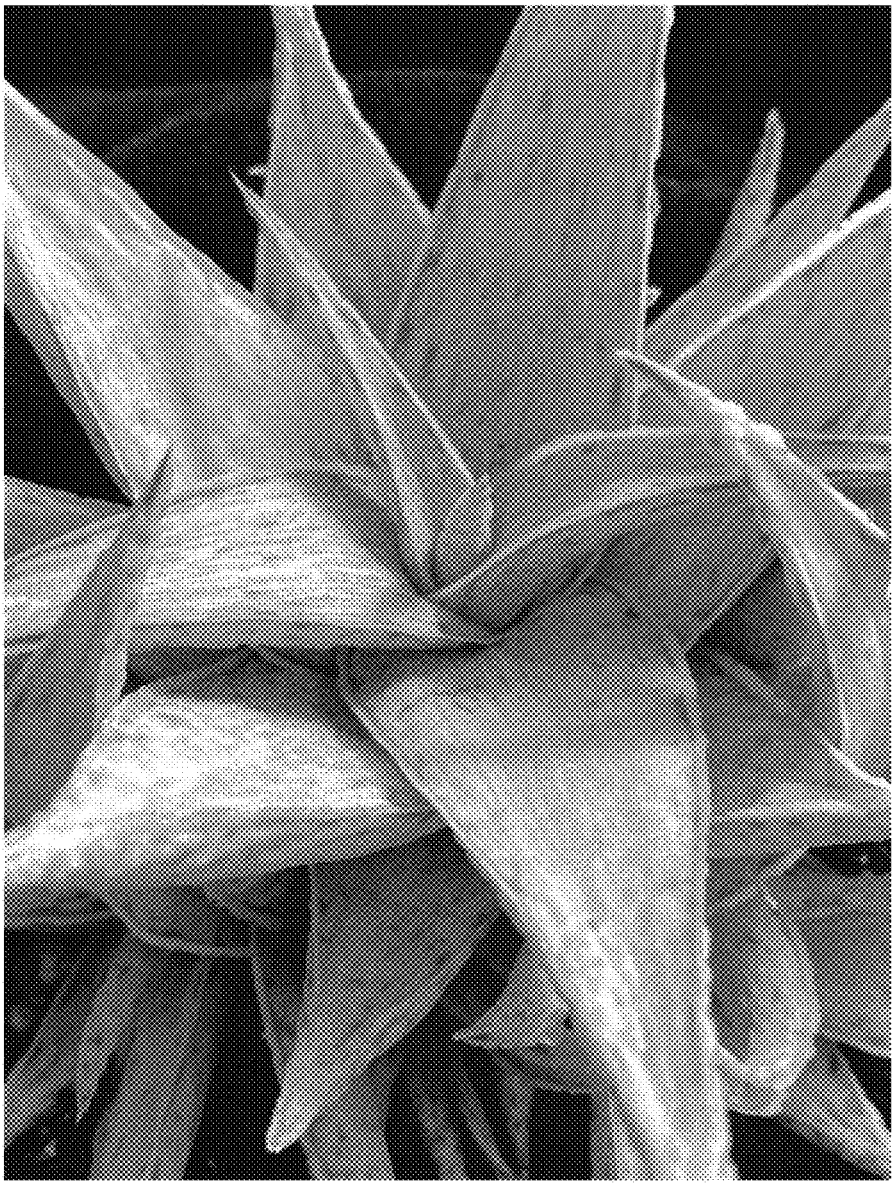

The accompanying photographs in FIG. 1 illustrate in full color a typical plant of 'SNOW DRIFT' grown in a greenhouse in Vista, Calif. This plant is approximately 20 months old, shown in a 1-gallon container.

Figure 2:
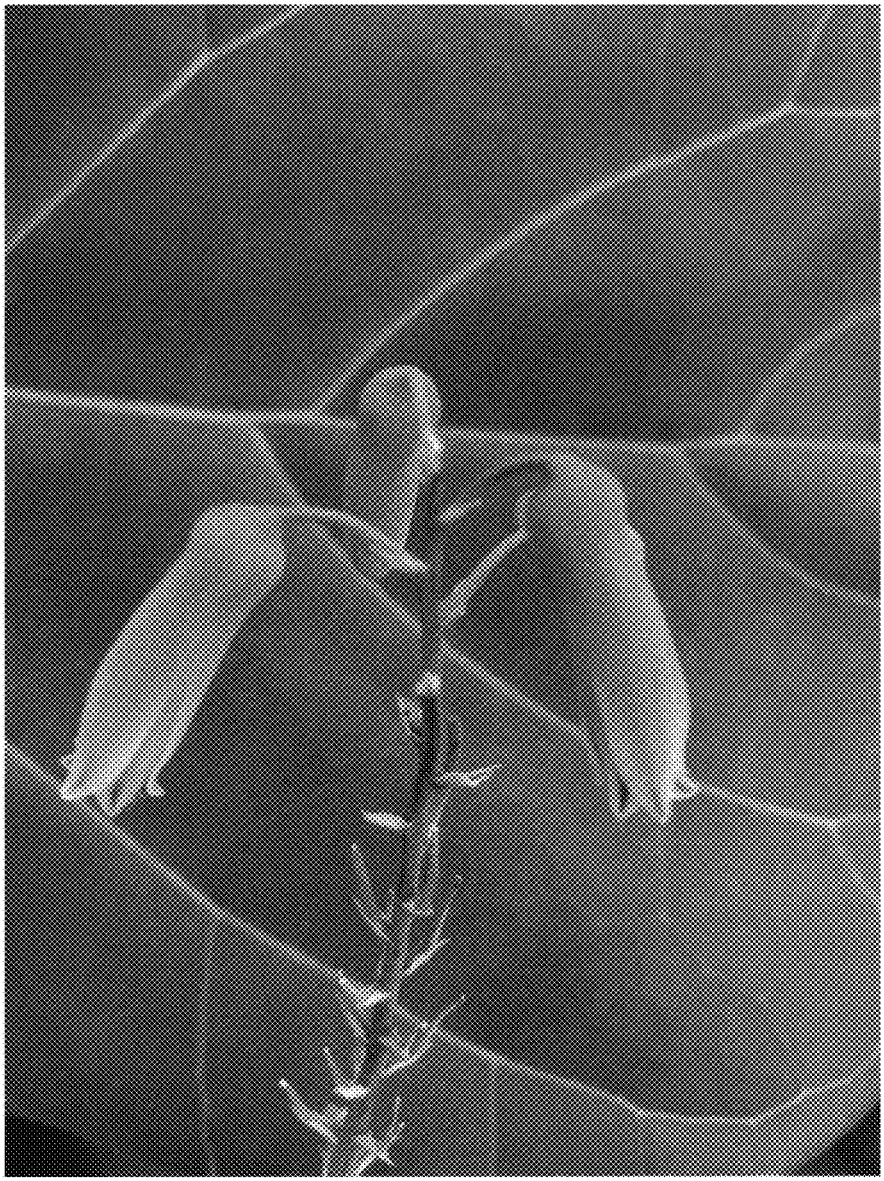

FIG. 2 illustrates the an ageing to nearly spent inflorescence of the new variety 'SNOW DRIFT' with 2 flowers remaining.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 edition, except where general terms of ordinary dictionary significance are used. The following observations and measurements describe 'SNOW DRIFT' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'SNOW DRIFT'.

Age of the plant described: 2 years.

PROPAGATION

Time to initiate roots: Approximately 30 days at 22° C.

Root description: Fibrous. Brown, not accurately measured with The R.H.S. Chart.

Propagation method: Tissue culture.

PLANT

Growth habit: Upright rosette, offsetting to form clumps with time.

Container size: 6 inches.

Height: Approximately 16 cm to top of highest leaf. Approximately 38 cm to top of highest inflorescence.

Plant spread: Approximately 20 cm.

Growth rate: Moderate.

Branching characteristics: Offsets from base.

FOLIAGE

Leaf:

- *Arrangement*.—Rosette.
- *Average length*.—Average 15-18 cm.
- *Average width*.—Average 5-6 cm.
- *Shape of blade*.—Lanceolate/deltoid.
- *Apex*.—Acuminate.
- *Base*.—Clasping.
- *Margin*.—Entire edge with no teeth.
- *Texture of top surface*.—Smooth.
- *Texture of bottom surface*.—Smooth.
- *Quantity of leaves per plant*.—Average 10.
- *Color*.—Young foliage upper side: Near RHS Greyed-Green 198B, bar-shaped sparse blotches near Green 138B. Margin lightly flushed Red 49A. Young foliage under side: Near RHS Greyed-Green 198B, bar-shaped sparse blotches near Green 138B. Margin lightly flushed Red 49A. Mature foliage upper side: Near RHS Greyed-Green 198B, bar-shaped sparse blotches near Green 138B. Margin lightly flushed Red 49A. Mature foliage under side: Near RHS Greyed-Green 198B, bar-shaped sparse blotches near Green 138B. Margin lightly flushed Red 49A.
- *Venation*.—Linear. Color: Indistinguishable from leaf blade.

FLOWER

Natural flowering season: Rebloomer, three to four times a year.

Inflorescence type and habit: Panicle, seldom branched.

Rate of flower opening: Moderate, successive.

Flower longevity on plant: 1.5 months.

Quantity of flowers: 10 to 20.

Total inflorescence size:

- *Height*.—Approximately 30 cm.
- *Width*.—Approximately 7 cm.

Corolla:

- *Arrangement*.—Perianth cylindrical/corolla small and reflexed.
- *Length*.—Approximately 2.5 cm.
- *Width*.—Approximately 1 cm at widest point.
- *Tepals*.—Typically fused, the most mature flowers split at apex into 6 tepals/lobes. Unfused portion about 8 mm long and 4 mm wide. Unfused portion longer with age, about 1.1 cm with age.
- *Color*.—Tepals: When opening: Outer surface: Near RHS Red 44A. Inner surface: Near RHS Yellow 2D. Fully opened: Outer surface: Near RHS Red 44B. Inner surface: Near RHS Yellow 2D.

Bud:

- *Shape*.—Cylindrical.
- *Length*.—Approximately 2.5 cm.
- *Diameter*.—Approximately 0.5 cm.
- *Color*.—Near RHS Red 44A.

Peduncle:

- *Length*.—Approximately 22 cm.
- *Width*.—About 7 mm.
- *Color*.—Near Greyed-Purple N187C.

Pedicels:

- *Length*.—Approximately 1 cm.
- *Width*.—2 mm.
- *Aspect*.—Lateral.
- *Color*.—Near RHS Red 44D.

Fragrance: None.

REPRODUCTIVE ORGANS

Stamens:

- *Number*.—6.
- *Filament length*.—Approximately 2.5 cm.
- *Filament color*.—Near RHS White N155B.
- *Anther length*.—0.25 cm.
- *Anther color*.—Near RHS Yellow 6B.
- *Anther shape*.—Oval.
- *Pollen color*.—Near RHS Yellow 10A.

Pistil:

- *Number*.—1.
- *Length*.—Approximately 3 cm.
- *Style color*.—Near RHS White N155B.
- *Stigma*.—Shape: Rounded. Color: Near RHS White N155B. Ovary color: Near RHS Greyed-Green 193D.

OTHER CHARACTERISTICS

Seeds and fruits: Pods about 10 mm long and 5 mm wide, colored near Green 137D when immature, ripening to Grey-Brown N199D. Seed dust like, colored near Grey-Brown 199C.

Temperature tolerance: Tolerates temperatures from approximately 0° to at least 35° C.

Disease/pest resistance: Shows mite resistance and black spot resistance (pathogen unconfirmed).

What is claimed is:

1. A new and distinct cultivar of *Aloe* plant named 'SNOW DRIFT' as herein illustrated and described.

* * * * *